United States Patent [19]
Brodeur

[11] Patent Number: 5,370,637
[45] Date of Patent: Dec. 6, 1994

[54] COLLAPSIBLE FEMALE URINATION AID

[76] Inventor: Joseph P. Brodeur, 11 Carpenter Rd., Dudley, Mass. 01571

[21] Appl. No.: 239,574

[22] Filed: May 9, 1994

[51] Int. Cl.$^5$ .............................................. A61F 5/44
[52] U.S. Cl. ........................................ 604/329; 4/144.3
[58] Field of Search .............................. 604/327–331; 4/144.1–144.3

[56] References Cited

U.S. PATENT DOCUMENTS

| | | | |
|---|---|---|---|
| 901,134 | 10/1908 | Weidl | 4/144.3 |
| 3,194,238 | 7/1965 | Breece, Jr. | 604/329 |
| 4,756,029 | 7/1988 | Zieve et al. | 604/329 |

FOREIGN PATENT DOCUMENTS 8701581  3/1987  WIPO .................. 604/328

Primary Examiner—Jerome L. Kruter
Attorney, Agent, or Firm—Michael J. Colitz, Jr.

[57] ABSTRACT

A urination aid for facilitating urination by females in a substantially upright position. The device includes a base having a center opening which may be positioned over the female genital region. A collapsible fluid guide extends from the base to guide urine directed through the center opening of the base away from the user. A pair of raised finger pads are disposed along lateral edges of the base and allow for increased application of pressure to a seal extending around the central opening. An absorbent pad is secured to a lower end of the base and may be used as a sanitary wipe after urination.

6 Claims, 4 Drawing Sheets

COLLAPSIBLE FEMALE URINATION AID

BACKGROUND OF THE INVENTION

1. Field of the Invention

The present invention relates to urinal devices and more particularly pertains to a collapsible female urination aid for facilitating urination by females in a substantially upright position.

2. Description of the Prior Art

The use of urinal devices is known in the prior art. More specifically, urinal devices heretofore devised and utilized for the purpose of facilitating female urination are known to consist basically of familiar, expected and obvious structural configurations, notwithstanding the myriad of designs encompassed by the crowded prior art which have been developed for the fulfillment of countless objectives and requirements.

For example, a funnel device to facilitate urination by women in an upright position is illustrated in U.S. Pat. No. 5,091,998 which includes a semi-rigid funnel rim contoured to surround the female genital region with a flexible funnel body depending from the rim. The funnel body has a continuous wall sloped inwardly and towards the front of the funnel body which terminates in an orifice situated towards the front of the funnel body. A bendable, elongated disposable tube is sealably attached to the funnel orifice and is inclined downward and outward at an angle with regard to the funnel body.

Another patent of interest is U.S. Pat. No. 4,751,751 which teaches a disposable urinating funnel for females which comprises a thin, paper-like sheet which is folded in half to form two overlapping sections whose free edges are connected together and tapered towards the fold line to form a flunnel-like shape. The upper edges of the funnel-shape are curved to cover a female vaginal area, and the opposite, bottom edges form a spout-like portion.

Other known prior art urinal devices include U.S. Pat. No. 4,936,838; U.S. Pat. No. 4,626,249; and U.S. Pat. Des. No. 290,880.

While these devices fulfill their respective, particular objectives and requirements, the aforementioned patents do not disclose a urination aid for facilitating urination by females in a substantially upright position which includes a base having a center opening which may be positioned over the female genital region with a collapsible fluid guide extending from the base to guide urine directed through the center opening of the base away from the user, such that the collapsible fluid guide may be compactly stored against the base to form a substantially flat package. Furthermore, none of the known prior art urinal devices teach or suggest a collapsible female urination aid of the aforementioned structure which further includes a pair of raised finger pads disposed along lateral edges of the base for permitting increased application of pressure to a seal extending around the central opening, as well as an absorbent pad secured to a lower end of the base for performing a sanitary wiping of the genital area after urination.

In these respects, the collapsible female urination aid according to the present invention substantially departs from the conventional concepts and designs of the prior art, and in so doing provides an apparatus primarily developed for the purpose of facilitating urination by females in a substantially upright position.

SUMMARY OF THE INVENTION

In view of the foregoing disadvantages inherent in the known types of urinal devices now present in the prior art, the present invention provides a new collapsible female urination aid construction wherein the same can be utilized for facilitating urination by females in a substantially upright position. As such, the general purpose of the present invention, which will be described subsequently in greater detail, is to provide a new collapsible female urination aid apparatus and method which has many of the advantages of the urinal devices mentioned heretofore and many novel features that result in a collapsible female urination aid which is not anticipated, rendered obvious, suggested, or even implied by any of the prior art urinal devices, either alone or in any combination thereof.

To attain this, the present invention generally comprises a urination aid for facilitating urination by females in a substantially upright position. The device includes a base having a center opening which may be positioned over the female genital region. A collapsible fluid guide extends from the base to guide urine directed through the center opening of the base away from the user. A pair of raised finger pads are disposed along lateral edges of the base and allow for increased application of pressure to a seal extending around the central opening. An absorbent pad is secured to a lower end of the base and may be used as a sanitary wipe after urination.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new collapsible female urination aid apparatus and method which has many of the advantages of the urinal devices mentioned heretofore and many novel features that result in a collapsible female urination aid which is not anticipated, rendered obvious, suggested, or even implied by any of the prior art urinal devices, either alone or in any combination thereof.

It is another object of the present invention to provide a new collapsible female urination aid which may be easily and efficiently manufactured and marketed.

It is a further object of the present invention to provide a new collapsible female urination aid which is of a durable and reliable construction.

An even further object of the present invention is to provide a new collapsible female urination aid which is susceptible of a low cost of manufacture with regard to both materials and labor, and which accordingly is then susceptible of low prices of sale to the consuming public, thereby making such collapsible female urination aids economically available to the buying public.

Still yet another object of the present invention is to provide a new collapsible female urination aid which provides in the apparatuses and methods of the prior art some of the advantages thereof, while simultaneously overcoming some of the disadvantages normally associated therewith.

Still another object of the present invention is to provide a new collapsible female urination aid for facilitating urination by females in a substantially upright position.

Yet another object of the present invention is to provide a new collapsible female urination aid which includes a base having a center opening positionable over the female genital region, with a collapsible fluid guide extending from the base to guide urine directed through the center opening of the base away from the user.

Even still another object of the present invention is to provide a new collapsible female urination aid which includes a pair of raised finger pads disposed along lateral edges of the base to facilitate increased application of pressure to a seal extending around the central opening of the base.

Even still yet another object of [he present invention is to provided a new collapsible female urination aid which further includes an absorbent pad secured to a lower end of the base which may be utilized as a sanitary wipe after urination.

Even still yet a further object of the present invention is to provide a new collapsible female urination aid which may be stored within a substantially flat package and constructed of disposable materials.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
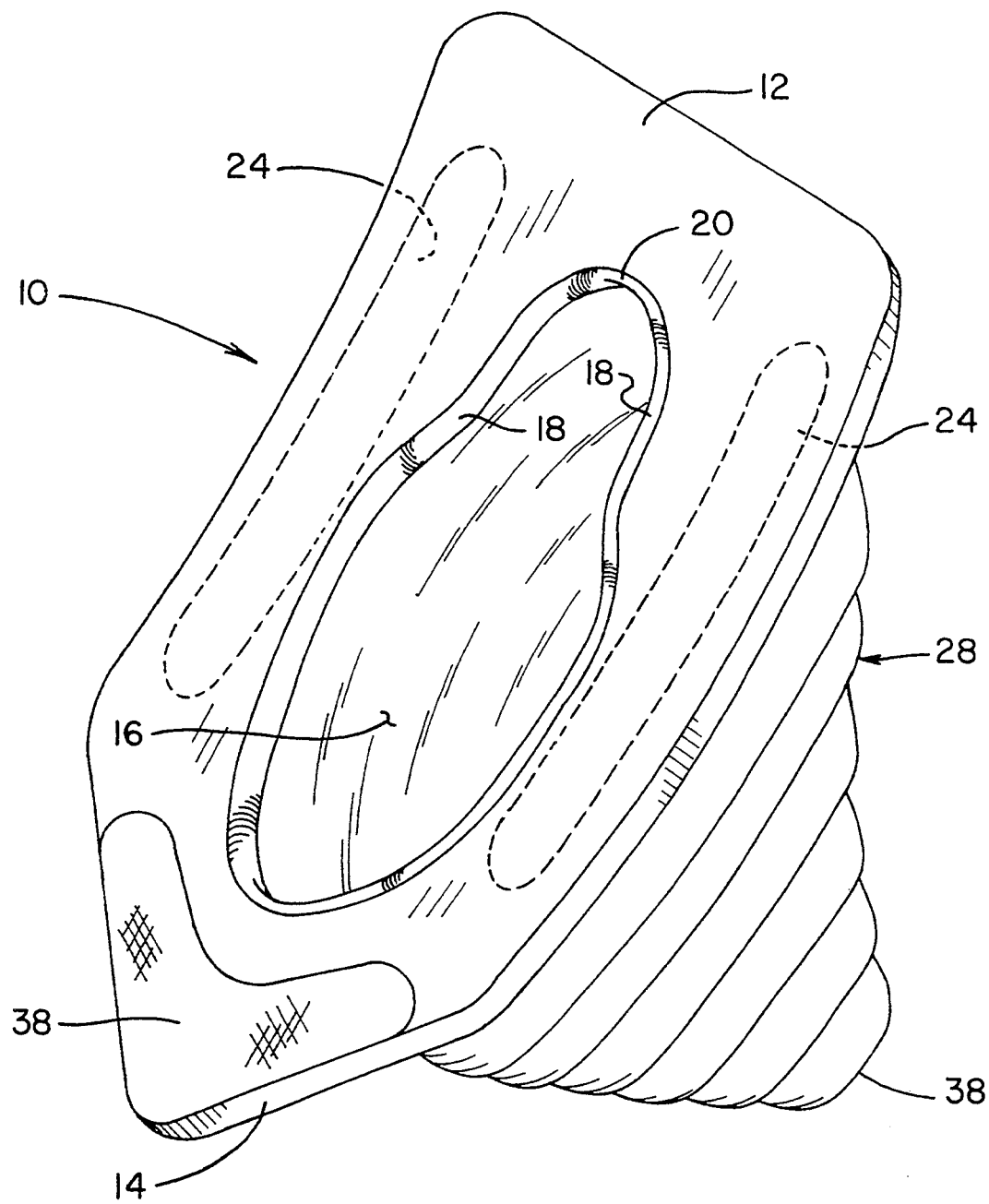
FIG. 1 is an isometric illustration of a collapsible female urination aid comprising the present invention.

With reference now to the drawings, and in particular to FIGS. 1-6 thereof, a new collapsible female urination aid embodying the principles and concepts of the present invention and generally designated by the reference numeral 10 will be described.

Figure 3:
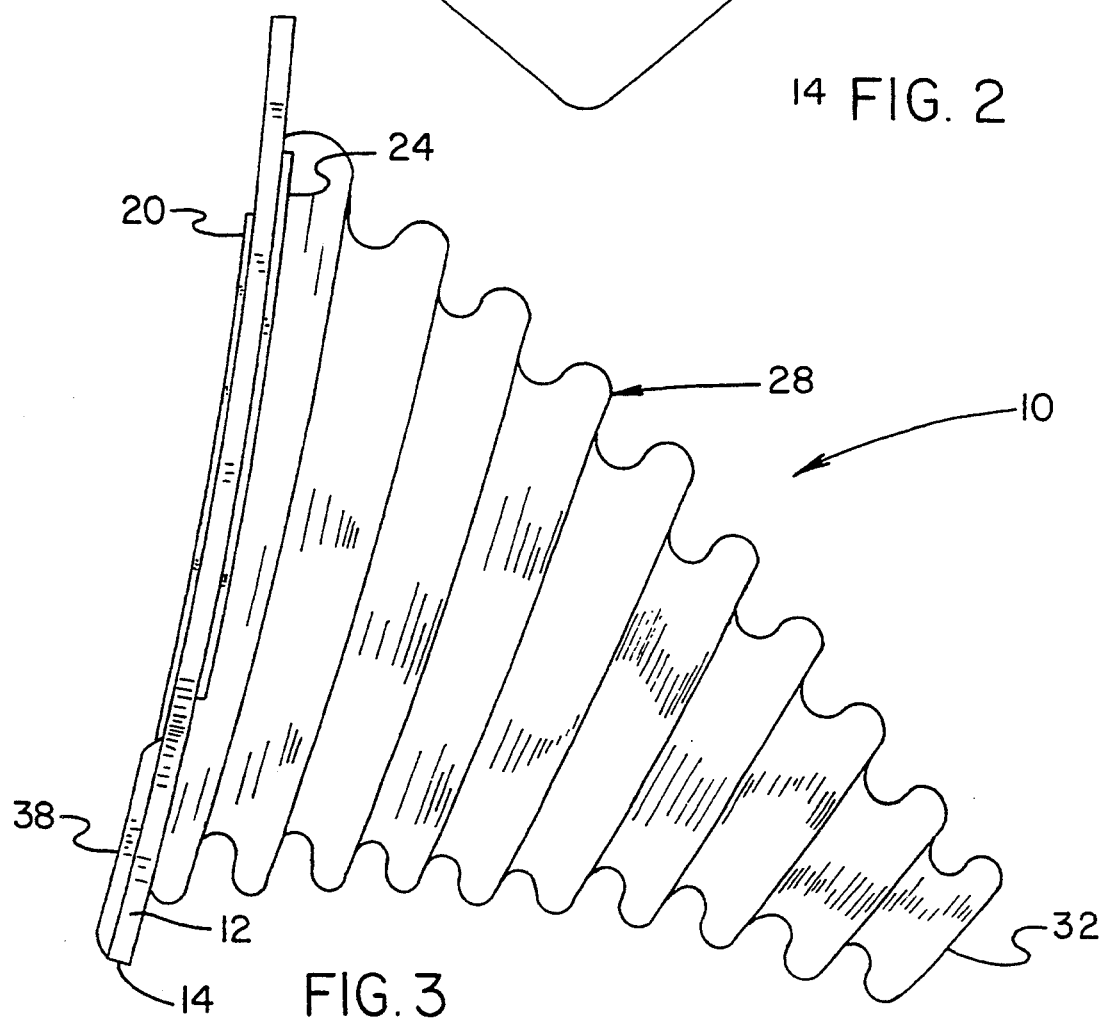
FIG. 3 is a side elevation view of the invention.

More specifically, it will be noted that the collapsible female urination aid 10 comprises a substantially rectangular base 12 having a V-shaped end 14 and a slightly arcuate shape, as illustrated in FIGS. 1 and 3 of the drawings. The base 12 is formed of a substantially resilient, deformable material and dimensioned to fit between the legs and over the anterior genital area of a female. A substantially oval center opening 16 is directed through the base, with a longitudinal dimension of the center opening being aligned with a longitudinal dimension of the base, as illustrated in FIG. 1. The center opening 16 is contoured to extend around the vulva of the human female genital area and is provided with a pair of upper contours 18 which substantially reduce a transverse diameter of the center opening to more closely follow the contours of the genital region. A seal 20 circumscribes the center opening 16, including the upper contours 18, and projects slightly above the engaging face 22 of the base 12, as illustrated in the top plan view of FIG. 5. Thus, the seal 20 effectively engages the labia and other areas of the vagina to form a substantially fluid-tight seal when the engaging face 22 of the base 12 is positioned against the human female genital region.

Figure 2:
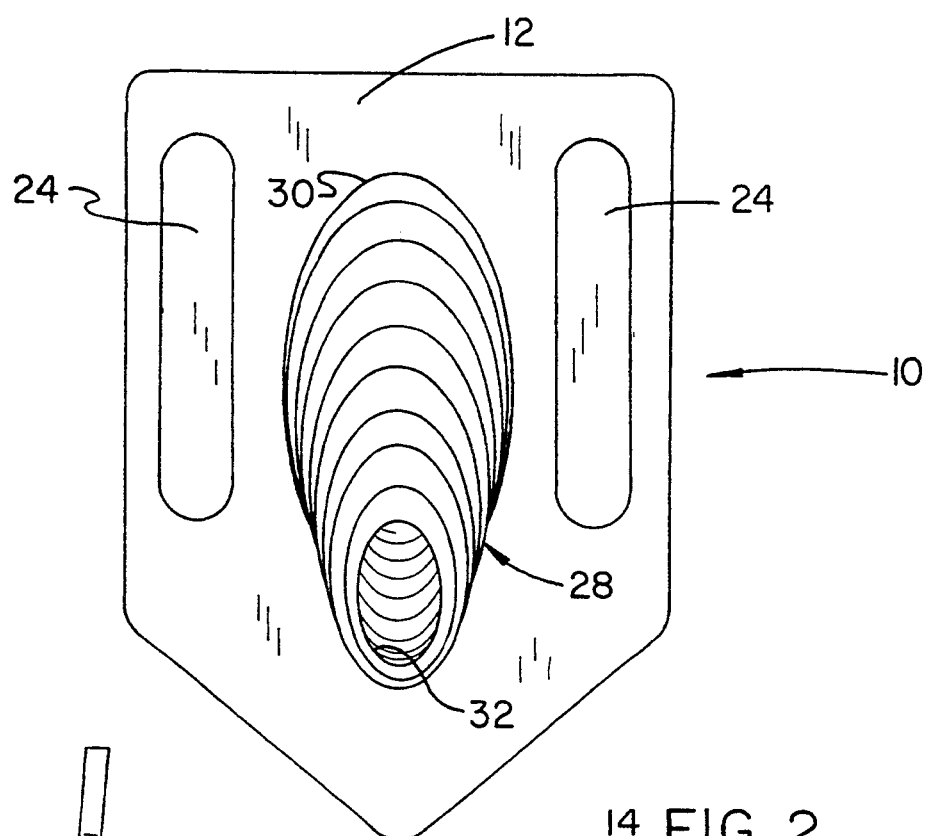
FIG. 2 is a front elevation view of the present invention.

To hold the base 12 against the female genital region, the fingers of the individual using the device 10 may be positioned on opposed sides of the center opening 16, whereby sealing pressure against the genital area may be imparted through the base 12. To facilitate increased application of pressure to the genital area, as well as reduced deformation of the base 12, a pair of finger pads 24 extend along laterally opposed sides of the center opening 16, as best illustrated in FIG. 2. Thus, the individual using the urination aid 10 may position two or more fingers of a single hand into engagement with the finger pads 24 to create a substantially fluid-tight seal as discussed above. Alternatively, two or more digits of opposed hands of the individual may be positioned on each finger pad. Thus, the device 10 may be comfortably held in place by either one or two hands.

Figure 5:
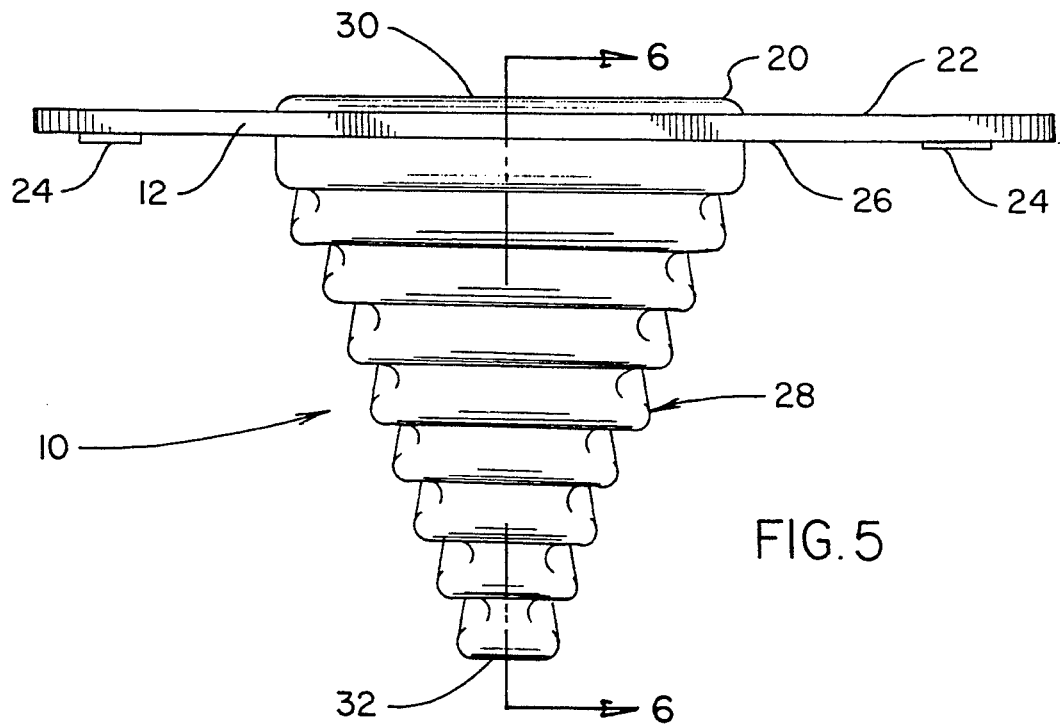
FIG. 5 is a top plan view of illustrating the collapsible fluid guide in an extended position.
Figure 6:
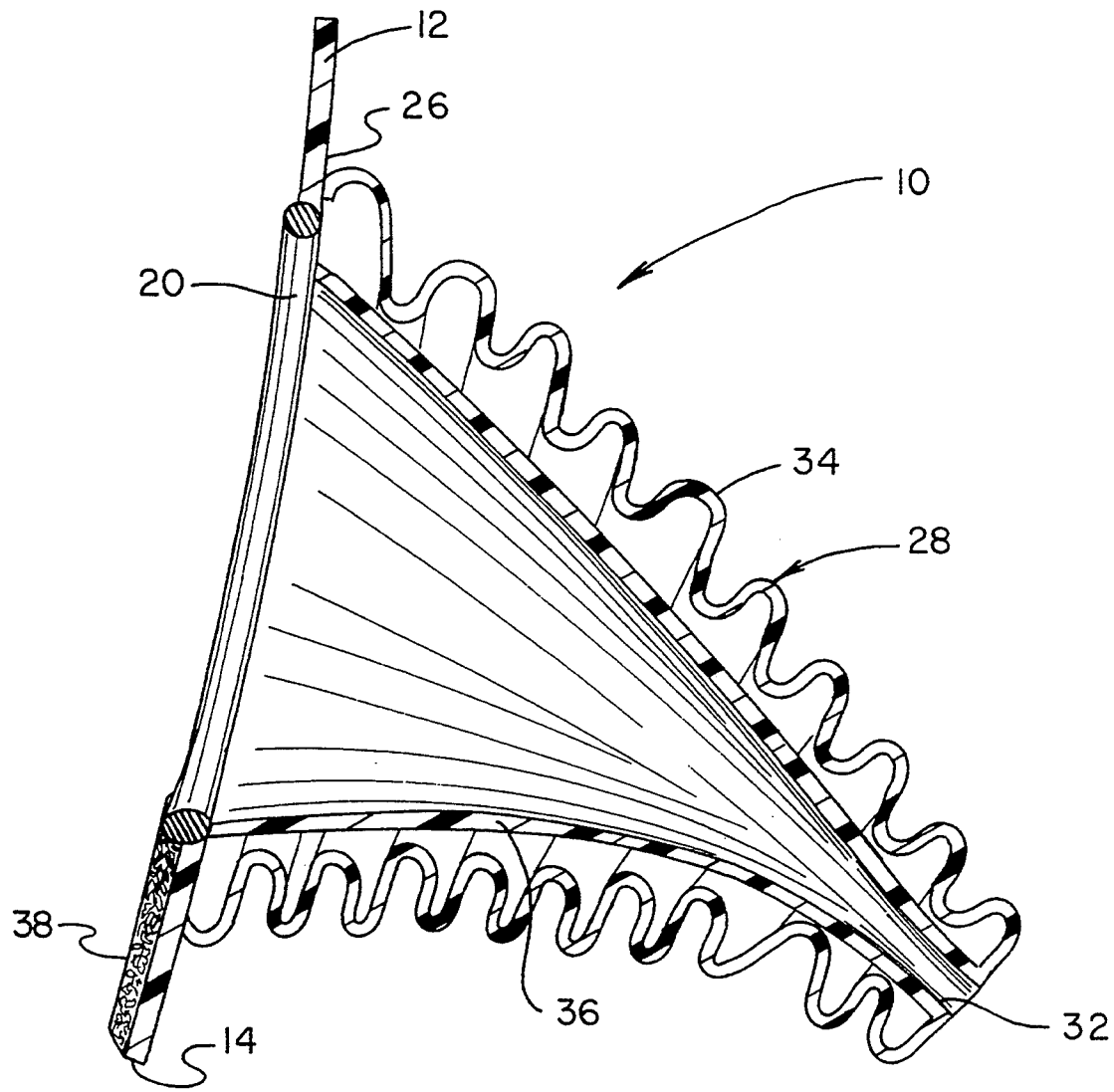
FIG. 6 is a cross sectional view taken along line 6—6 of FIG. 5.

Extending from an outward face 26 of the base 12 is a collapsible fluid guide 28 having an inlet 30 and an outlet 32, as illustrated in FIGS. 2 and 5. The collapsible Guide 28 is formed of a substantially deformable material and, therefore, may be manipulated into various positions such that urine directed through the center opening 16 and the inlet 30 is expelled through the outlet 32 in a desired trajectory. The cross section view of FIG. 6 most clearly illustrates the construction of the collapsible fluid guide 28, and it can be seen from this Figure that the collapsible fluid guide comprises an exterior accordion boot 34 having a plurality of contours which allow for extension and compression of the boot. The accordion boot 34 is coupled to the outer face 26 of the base 12 and is provided with a resilient inner liner 36 which extends concentrically through the boot. The inner liner 36 is formed of a substantially deformable material, such as plastic, latex, or other similar equivalents thereof, and is coupled to the outer face 26 of the base 12 within the boot 34. In addition, the inner liner 36 is coupled to an outer distal end of the accordion boot 34 at the outlet 32. The accordion boot 34 and the inner liner 36 may be integrally formed or, alternatively, the accordion boot may be formed separate from the inner liner. To this end, the accordion boot 34 may be constructed of a substantially deformable metallic material, such as aluminum or the like, which will retain a position upon deformation thereof, with the inner liner 36 being formed of any substantially water impermeable material, including plastics, latex, wax paper, or treated fabrics. Thus, the accordion boot 34, should it be constructed of such a metallic material, may be adjusted to a desired position whereby the nature of the material will retain such position.

Figure 4:
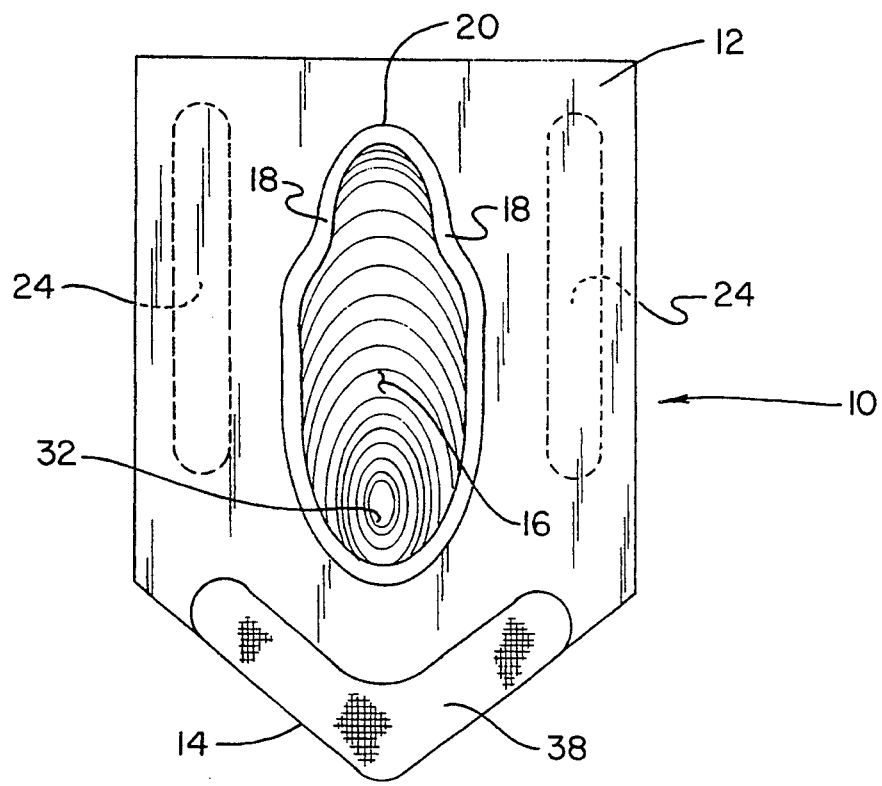
FIG. 4 is a rear elevation view detailing the absorbent pad and the central opening of the base.

An absorbent pad 38 is coupled to the engaging face 22 of the base 12 and extends along the contour of the V-shaped end 14, as best illustrated in FIGS. 1 and 4. The absorbent pad 38 is positioned upon the base 12 so as to be located immediately beneath the female genital area when the engaging face 22 of the base 12 is positioned thereagainst. Thus, after urination, the device 10 may be lifted upwardly to engage the absorbent pad 38 to the vagina to perform a wiping of the area. To this end, the absorbent pad 38 may be constructed of any fabric or absorbent material, such as tissue paper or the like. In addition, the absorbent pad 38 may be impregnated with germicidal compositions and/or deodorizing compositions to impart a freshening to the area being wiped.

The collapsible female urination aid 10 is constructed so as to be collapsible into a substantially flat package, i.e. the fluid guide 28 may be compressed against the base 12, such that the entire device 10 may be stored within an envelope. The urination aid 10 may be constructed of entirely disposable materials, whereby it is discarded after use or, alternatively, the device 10 may be constructed of reusable materials and simply washed thoroughly after use.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new collapsible female urination aid comprising:
   a base having a slightly arcuate shape with a lower end, an engaging face, and an outer face, said base being dimensioned to fit between a pair of legs and over an anterior genital area of a female, said base further having a center opening directed therethrough;
   a pair of finger pads extending along laterally opposed sides of said center opening of said base, said finger pads being operable to facilitate an increased application of pressure to said base; and,
   a collapsible fluid guide having an inlet and an outlet, said fluid guide being coupled to said outer face of said base and in fluid communication with said center opening, said fluid guide comprising an exterior accordion boot having a plurality of contours which allow for extension and compression of said boot, and a resilient inner liner extending concentrically through said boot, with said inner liner being coupled to said outer face of said base within said boot and further being coupled to said boot at said outlet, whereby urine directed through said center opening is expelled through said fluid guide outlet.

2. The new collapsible female urination aid of claim 1, and further comprising an absorbent pad coupled to said lower end of said engaging face of said base, said absorbent pad being operable such that, after urination, said urination aid is lifted upwardly to engage said absorbent pad to said genital area to perform a wiping of said area.

3. The new collapsible female urination aid of claim 2, wherein said accordion boot is constructed of a deformable material which will retain a position upon deformation thereof, such that said boot is adjustable to a desired position, whereby said material will retain such position.

4. The new collapsible female urination aid of claim 3, wherein said absorbent pad comprises an absorbent material impregnated with a germicidal compositions to impart a disinfecting of said area being wiped.

5. A new collapsible female urination aid comprising:
   a base having a slightly arcuate shape with a lower end, an engaging face, and an outer face, said base being dimensioned to fit between a pair of legs and over an anterior genital area of a female, said base further having a center opening directed therethrough;
   a seal circumscribing said center opening and projecting slightly beyond said engaging face of said base, said seal being operable to form a substantially fluid-tight seal when said engaging face of said base is positioned against said genital area;
   a pair of finger pads extending along laterally opposed sides of said center opening of said base, said finger pads being operable to facilitate an increased application of pressure to said base;
   a collapsible fluid guide having an inlet and an outlet, said fluid guide being coupled to said outer face of said base and in fluid communication with said center opening, said fluid guide comprising an exterior accordion boot having a plurality of contours which allow for extension and compression of said boot, and a resilient inner liner extending concentrically through said boot, with the inner liner being coupled to said outer face of said base within said boot and further being coupled to said boot at said outlet, whereby urine directed through said center opening is expelled through said fluid guide outlet, said accordion boot being constructed of a deformable material which will retain a position upon deformation thereof, such that said boot is adjustable to a desired position, whereby said material will retain such position; and, an absorbent pad coupled to said lower end of said engaging face of said base, said absorbent pad being operable such that, after urination, said urination aid is lifted upwardly to engage said absorbent pad to said genital area to perform a wiping of said area.

6. The new collapsible female urination aid of claim 5, wherein said center opening is provided with a pair of upper contours which substantially reduce a transverse diameter of said center opening to more closely follow a contour of said genital area.

* * * * *